United States Patent
Adeyeye et al.

[11] Patent Number: 6,156,340
[45] Date of Patent: Dec. 5, 2000

[54] ORALLY ADMINISTRABLE TIME RELEASE DRUG CONTAINING PRODUCTS

[75] Inventors: Christianah Moji Adeyeye, Mt. Lebanon, Pa.; Hideki Ichikawa; Yoshinobu Fukumori, both of Kobe, Japan

[73] Assignee: Duquesne University of the Holy Ghost, Pittsburgh, Pa.

[21] Appl. No.: 08/624,997

[22] Filed: Mar. 29, 1996

[51] Int. Cl.[7] ............................. A61K 9/58; A61K 9/32
[52] U.S. Cl. ..................... 424/463; 424/474; 424/482
[58] Field of Search .................................. 424/439, 451, 424/464, 474, 463, 482

[56] References Cited

U.S. PATENT DOCUMENTS

| | | | |
|---|---|---|---|
| 5,401,515 | 3/1995 | Woodard et al. | 424/475 |
| 5,472,710 | 12/1995 | Klollers-Bethke | 424/468 |
| 5,472,714 | 12/1995 | Bourquin | 424/472 |
| 5,541,170 | 7/1996 | Rhodes et al. | 514/166 |

FOREIGN PATENT DOCUMENTS 2203336 10/1988 United Kingdom .

OTHER PUBLICATIONS

Hirotani, Y. et al., "Preparation of Controlled–release Granules of Sodium Diclofenac", *Chem. Pharm. Bull.*, vol. 35, pp. 3049–3053 (1987).

Sagara, K. et al., "Bioavailability Study of Commercial Sustained–release Preparations of Diclofenac Sodium in Gastro–intestinal Physiology Regulated–dogs", *Chem. Pharm. Bull.*, vol. 40, pp. 3033–3306 (1992).

Ichikawa, H. et al., "Coating of Pharmaceutical Powders by fluidized Bed Process", *Chem. Pharm. Bull.*, vol. 42, pp. 1308–1314 (1994).

Gupta, V. K. et al., "Controlled Release Microspheres of Diclofenac Sodium Prepared by Spherical Crystallization Technique", *Pharmazie*, vol. 49, pp. 692–693 (1994).

Guterres, S. S. et al., "Poly(DL–lactide) Nanocapsules Containing Diclofenac: I. Formation and Stability Study", *Int. J. Pharm.*, vol. 113, pp. 57–63 (1995).

*Primary Examiner*—Raj Bawa
*Attorney, Agent, or Firm*—Diane R. Meyers; Arnold B. Silverman; Eckert Seamans Cherin & Mellott, LLC

[57] ABSTRACT

A time release orally administrable drug containing product comprising a core, a drug layer attached to the core, and first and second coating layers is disclosed. The first coating layer is directly adjacent to the drug layer, and has a limited permeability to water. The second coating layer is directly adjacent to the first coating, and is more permeable to water than the first layer. A method for using this drug in the treatment of a patient is also disclosed.

46 Claims, 2 Drawing Sheets

ORALLY ADMINISTRABLE TIME RELEASE DRUG CONTAINING PRODUCTS

BACKGROUND OF THE INVENTION

1. Field of the Invention

This invention relates to a method of treating a patient with an orally administrable time release drug product. In particular, it relates to a drug product that will be time released in a patient. The drug product may be used therapeutically, prophylactically and diagnostically for diseases wherein a general continuous level of drug concentration in the blood stream is desired.

2. Description of the Prior Art

It is known to provide orally administrable drugs in liquid suspensions, tablets and capsules. It is also known to provide a plurality of time-release drugs in treating, for example, the symptoms of a cold. One of the problems with the orally administrable drug form is the fact that the drug has a short half-life thereby requiring frequent administration of the drug in an effort to achieve the desired blood concentration. Another difficulty with frequent dosing is that the cycles of concentration cover a wide range which not only fails to produce a steady state of ingredients of drug but can give undesired side effects.

For the orally administrable non-steroidal anti-inflammatory drug, diclofenac sodium, commonly employed in the long term treatment of rheumatic disorders, many problems are known. This drug is typically completely absorbed following oral administration and its elimination half-life is 1 to 2 hours. Repeated oral administration of diclofenac sodium in long term therapy cases frequently causes gastrointestinal disturbances and may cause kidney failure. Due to the biopharmaceutical and pharmacological properties of the drug, a controlled time-release form is desirable. Gupta studied the controlled release of microspheres of diclofenac sodium prepared by spherical crystallization technique. Gupta, V. K., Jayaswal, S. B. Srivastava, A. K. and Kumar, M. V., "Controlled release microspheres of diclofenac sodium prepared by spherical crystallization technique." Pharmazie, 49 (1994) 692–693. Guterres investigated a formulation and stability study of Poly(DL-lactide) nanocapsules containing diclofenac. Guterres, S. S., Fessi, H., Barratt, G., Devissaguet, J. P. and Puisieux, F. "Poly(DL-lactide) nanocapsules containing diclofenac: I. Formation and stability study." Int. J. Pharm., 113 (1995) 57–63. Hirotani studied the preparation of controlled-release granules of sodium diclofenac. Hirotani, Y., Arakawa, Y., Maeda, Y. Yamaji, A., Kamada, A and Nishihata, T., "Preparation of controlled-release granules of sodium diclofenac." Chem. Pharm. Bull., 35 (1987) 3049–3053. Ichikawa has investigated the coating of pharmaceutical powders by a fluidized bed process. Ichikawa, H., Tokomutsu, H., Jono, K. Fukuda, T., Osako, Y and Fukomori, Y., "Coating of pharmaceutical powders by fluidized bed process. VI. microencapsulation using blend and composite lattices of copoly(ethyl acrylate-methyl methacrylate-2-hydroxyethyl methacrylate). Chem Pharm. Bull., 42 (1994) 1308–1314. Sagara has studied the bioavailability of commercial sustained-release preparations of diclofenac sodium in gastro-intestinal physiology related drugs. Sagara, K., Nagamatsu, Y., Yamada, I., Kawata, M., Mizuta, H. and Ogawa, K., "Bioavailability study of commercial sustained-release preparations of diclofenac sodium in gastro-intestinal physiology regulated-dogs." Chem. Pharm. Bull., 40 (1992) 3303–3306. Sagara's technology uses only one layer which is a methacrylic acid copolymer.

In spite of the prior art disclosures, there remains a very real and substantial need for a prolonged time-release drug and method of treating a patient with the drug that has prolonged time-release properties so that the desired steady state in the bloodstream will be achieved.

SUMMARY OF THE INVENTION

The present invention has met the hereinbefore described need. The present invention provides a time release orally administrable drug containing product comprising a core with a drug secured to the exterior of the core. A first coating having limited permeability to water is secured to the exterior of the drug. A second coating, which is more permeable to water than the first coating, is secured to the exterior of the first coating. The first and second coatings together comprise the time release components of the drug. The present invention also provides a method of treating a patient with an orally administrable time-release drug comprising securing the drug to the exterior of a core, creating time-release components of the drug by securing a first coating having limited permeability to water to the exterior of the drug, securing to the first exterior coating a second coating which is more permeable to water than is the first coating and administering a plurality of time-release components to a patient. The time-release components are in an aqueous suspension, tablet form, and capsule form. A first and second coating effect time release of the orally administrable drug within a patient for about 3 to 14 hours and preferably about 10 to 13 hours. It can be administered 2 to 4 times daily.

In a preferred embodiment, the first coating has a thickness of about 1.30 to 4.60 microns and a second coating has a thickness of about 6.70 to 13.40 microns. The time-release components have a substantially spherical configuration. The core is created with a diameter of about 19 to 57 microns. The time-release components have a diameter at the exterior of the first coating of about 60 to 77 microns. The time-release components have a diameter of 20 to 650 microns, preferably 50 to 250 microns when the time-release components are in liquid suspension form. The time-release components may be employed therapeutically, prophylactically and diagnostically. They can be employed therapeutically as an anti-inflammatory drug. They are used preferably in the treatment of rheumatic disorders selected from the group consisting of osteoarthritis, rheumatoid arthritis and ankylosing spondylitis.

The method also includes effecting dissolving the time-release components in vivo sequentially in acid, neutral and weak alkaline regions of the gastrointestinal tract. The method also employs an acidic polymeric dispersion coating as the first coating to prolong drug release. The method also employs as a core a material selected from the group consisting of calcium carbonate, sugar, dextrose and nonpareil seeds. The first coating is a material which retards rapid passage of water and the drug therethrough. The first coating is preferably an aqueous dispersion of Poly (methacrylic acid, ethyl acrylate) (commercially available under the designation Eudragit L30D-55). The method also includes employing as a second coat a latex acrylic polymer. The second coating is preferably Poly (ethyl acrylate, methyl methacrylate trimethylammonioethyl methacrylate chloride) (methacrylic acid, ethyl acrylate) (commercially available under the designation Eudragit RS-30D). The thickness of the second coating is established to achieve the desired time-release rate for the drug.

It is an object of this invention to provide an orally administrable time-release drug which effects the amount of the drug in the bloodstream at any one time and allows a general continuous level of drug concentration in the bloodstream.

It is an object of this invention to provide an oral suspension of a dosage form of this drug for ease of swallowing.

It is an object of this invention to provide prolonged release microcapsules and time-release components of this drug for use in a variety of dosage forms.

It is the object of this invention to construct a first coating which could suppress release of the desired drug even if the first coating is relatively thin.

It is also an object of this invention that the particle size of the time-release drug component be small enough to be stably suspended in some aqueous media.

It is also an object of this invention to have the release of the drug from time-release components or microcapsules to be prolonged at least up to adequate time required for twice a day administration.

These and other objects of the invention will be more fully understood from the drawing and the following description of the invention and the claims appended hereto.

DESCRIPTION OF THE PREFERRED EMBODIMENT

Figure 1:
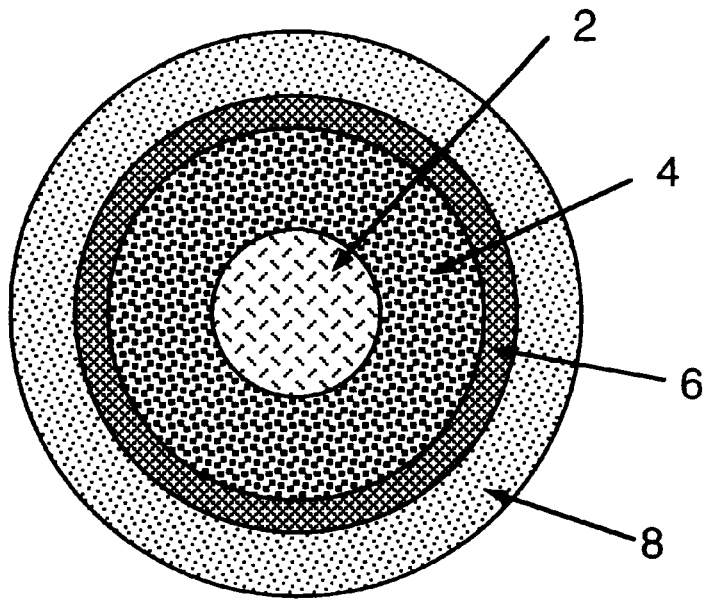
FIGS. 1 and 2 are cross-sectional diagrams of time-release components or microcapsules of the drug having Immediate Release (IR-MCS) and Prolonged Release (PR-MCS), respectively.

As used herein, the term "patients" means members of the animal kingdom including but not limited to human beings.

The present invention is directed to a time release drug formulation comprising: a core; a drug secured to the exterior of the core; a first coating having limited permeability to water secured to the exterior of the drug; and a second coating, which is more permeable to water than the first coating, secured to the exterior of the first coating; wherein the first and second coatings together comprise the time release components of the drug.

The core will generally have a diameter of about 19 to 57 microns. The core is generally comprised of an inert ingredient, preferably a material selected from the group consisting of calcium carbonate, sugar, dextrose and nonpareil seeds.

The drug layer is applied to the core layer. The drug is secured to the exterior of the core. Any suitable means can be used for applying the drug layer, including, for example, spraying a solution containing the drug onto the core. This solution can optionally contain a binder.

Attached to the drug layer is a first coating, which has a limited permeability to water and which retards rapid passage of an acidic drug and water. This first coating will typically have a diameter of between about 1.30 and 4.60 microns. The first coating is preferably an acidic polymeric dispersion coating which prolongs drug release, more preferably an aqueous dispersion of Poly(methacrylic acid, ethyl acrylate). Such a polymer is commercially available under the name Eudragit® L30D-55. The core, drug and first coating together typically have a diameter of between about 60 and 77 microns.

The second coating is more permeable to water than the first coating. The second coating typically has a diameter of between about 6.70 and 13.40 microns. Preferably, the second coating is a latex acrylic polymer, more preferably Poly(ethyl acrylate, methyl methacrylate trimethylammonioethyl methacrylate chloride). This polymer is commercially available under the trade name Eudragit® RS-30D.

The time release drug products of the present invention are preferably substantially spherical in configuration. The diameter of the time release drug products typically ranges between 20 and 650 microns, and is preferably between about 50 and 250 microns when the products are in a liquid suspension form.

It is a feature of the present invention that the time release drug containing products of the present invention, because of their size, can be suspended in an aqueous medium, thereby providing a liquid suspension which may be preferred by individuals who have difficulty swallowing tablets or capsules. Alternatively, the drug containing products of the present invention can be in either tablet or capsule form.

It will be appreciated that the first and second coatings together comprise the time release components of the drug containing product of the present invention. The first and second coatings together effect time release of the orally administrable drug within a patient over a maximum period of about 14 hours. It will be appreciated by those skilled in the art that the thickness of the second coating can be altered to achieve the desired time release rate for the drug. That is, the thickness of the second coating can be increased to achieve a longer period of time release in the body. The drug containing product is preferably administered twice daily.

The coatings work due to differential porosity. The inner coating is sensitive to pH. The outer coating acts only in a strict mechanical electrochemical sense. The inner coating functions both in a mechanical way due to porosity and in a chemical sense in that the pH of the water allows the water inside while the water and the drug permeates through the coating having an effect on the efficiency of the transportation therethrough. When the liquid is acidic, there will be a retarding effect on the flow rate or flux. It will be that the present invention provides in the first and second coating porosity such that water entering the time release component will pass through the second coating more rapidly that through the first coating and the drug and water exiting the time-release component will pass through the first coating more slowly than through the second coating. In the preferred form, passage through each coating will be by mechanical means with the passage through the first coating being augmented by ionic interaction.

In the preferred embodiment of this invention, calcium carbonate is used as the core, diclofenac sodium is the drug of choice, the first coating is Eudragit L30-55 and the second coating is Eudragit RS-30.

Figure 2:
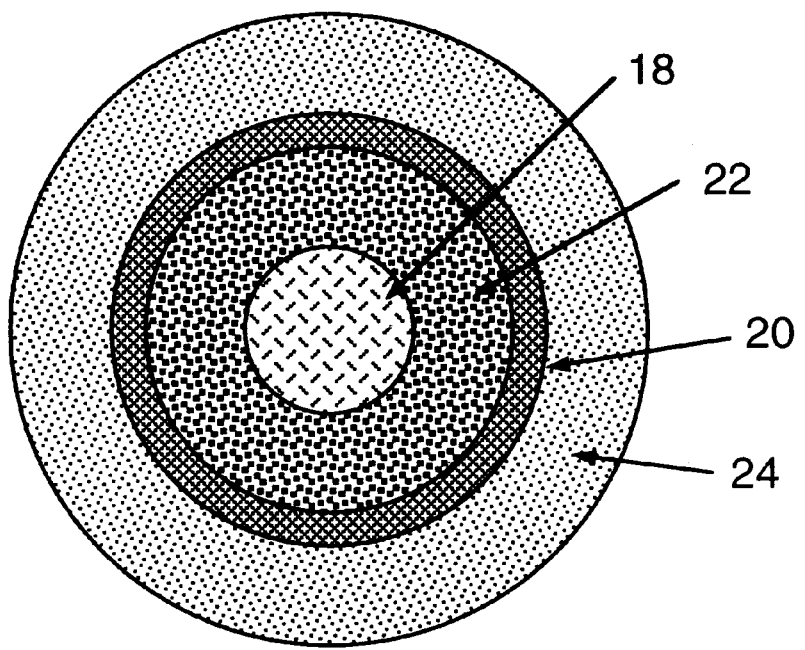

As illustrated in FIG. 1, one embodiment of the drug containing product of the present invention comprises a core 2 having a drug 4 secured to the exterior of the core 2. A first coating 6 surrounds the drug 4; a second coating 8 surrounds the first coating 6. Similarly, FIG. 2 shows a second embodiment of the present invention in which a core 18 is surrounded by drug layer 22, which is surrounded by first coating 20 and second coating 24. As can be seen by comparing the two figures, the second coating 8 of FIG. 1 and the second coating 24 of FIG. 2 are of varying thickness relative to the first coating, the drug layer and the core. This serves to illustrate that the second layer of the drug containing product of the present invention can be varied depending on the needs of the user. The drug containing product depicted in FIG. 1, with its thinner second coating 8, would therefore represent a drug having fast release or immediate release, whereas the drug containing product depicted in FIG. 2, with its thicker second coating 24, would have a more prolonged release action.

The present invention is also directed to a method of treating a patient with an orally administrable time release drug comprising administering to the patient a plurality of time release drugs comprising a core; a drug secured to the exterior of said core; a first coating having limited permeability to water secured to the exterior of the drug; and a second coating, which is more permeable to water than the first coating, secured to the exterior of the first coating; wherein the first and second coatings together comprise the time release components of the drug. The core, drug, and first and second coatings as used in the methods of the present invention are as described above.

The time release drug containing product can be administered to a patient in numerous forms. For example, the drug containing product can be suspended in an aqueous medium, or can be in either tablet or capsule form. Administration of the drug is preferably twice daily. The methods can be employed to treat a patient therapeutically, prophylactically and/or diagnostically. For example, the methods may be employed therapeutically as an anti-inflammatory drug. Preferably this use would include the treatment of rheumatic disorders such as osteoarthritis, rheumatoid arthritis and ankylosing spondylitis. It is within the scope of the present invention, however, to provide such methods for the treatment of numerous other diseases.

The method also includes effecting dissolving the time release components in vivo sequentially in the acid, neutral and weak alkaline regions of the gastrointestinal tract.

EXAMPLE I

An NQ-GM spouted bed coater equipped with a draft tube, a pneumatic spray nozzle with a liquid outlet caliber of 1.0 mm and a peristaltic pump was used. A laminated bag-filter with about an 1 μm opening and a filter with a 5 μm opening were set for drug-layering and coating, respectively.

To produce drug-layered particles, 50 grams of drug dispersed in binder solution of 500 ml was sprayed onto 25 grams of calcium carbonate cores charged into the coating chamber. Then, 25 grams of the obtained drug-layered particles were undercoated with Poly(methacrylic acid, ethyl acrylate) (commercially available under the designation Eudragit L30D-55) up to 12.5% coating levels (based on core weight) and subsequently coated with Poly(ethyl acrylate, methyl methacrylate trimethylammonioethyl methacrylate chloride (commercially available under the designation Eudragit RS-30D) up to 20% coating levels or 50% levels. Thus, two kinds of time-release components or microcapsules with different coating levels of Eudragit RS-30D were obtained. A schematic diagram of the cross-sectional structure of both time-release components or microcapsules are shown in FIG. 1 and FIG. 2.

FIG. 1 shows the schematic diagram of the cross-sectional structure of time-release components or microcapsules with immediate release (IR-MCS) and FIG. 2 shows time-release components or microcapsules with prolonged release (PR-MCS).

In FIG. 1 the core 2 has a drug 4 secured to the exterior of the core. Secured to the drug 4 is a first coating 6 having limited permeability to water and secured to the first exterior coating 6 is a second coating 8 which is more permeable to water than the first coating 6. This unit is an immediate release component of the orally administrable time-release drug.

In FIG. 2 the core 18 has a drug 22 secured to the exterior of the core. Secured to drug 22 is a first coating 20 having limited permeability to water and secured to the first exterior coating 20 is a second coating 24 which is more permeable to water than the first coating 22. This unit is a prolonged release component of the orally administrable time-release drug.

The sieve analysis was performed to analyze the size of the time-release components or microcapsules. For the drug-layered particles, an air jet sieve (alpine 200LS), equipped with a microsieve was operated at a charged weight of 3 grams, and the sieving was repeated until a constant weight was reached after 2 minutes of operation. For the time-release components or microcapsules, a row-tap shaker was used; the shaking time was 10 minutes and the charged weight was 10 grams.

Assays of the drug content in time-release components or microcapsules were carried out by pulverizing time-release components or microcapsules in a mortar and pestle and placing 10 mg of the powder in a glass tube containing 8 ml of dissolution fluid, sonicating for 30 minutes, centrifuging at 3000 rpm for 15 minutes, filtering with a 0.22 μm filter and spectrophotometrically measuring the UV absorbance of the diluted portion at 276 nm. The measured drug content was also used to estimate the value of 100% release in dissolution tests and the layering efficiency.

For drug-layered particles, the yield and drug content were 95% and 55%, respectively, and their mass median diameter was 71 μm. By coating of the drug-layered particles, their mass median diameter increased up to 94 μm for microcapsules 50% coated with Eudragit RS-30D. The drug content in the obtained time-release components or microcapsules was more than 30%.

Layering efficiency was estimated by calculating the measured content of diclofenac sodium in drug-layered particles multiplied by the total amount of produced drug-layered particles and divided by the charged amount of drug.

The release studies were performed on an NTR-VS6P dissolution apparatus by the JP XII paddle method at 200 ppm and 37 C. JP XII disintegration 2nd fluid (pH 6.8) was used as a dissolution fluid. The prepared microcapsules were dried in a vacuum at room temperature for 12 hours. To make a film-formation complete, these time-release components or microcapsules were mixed with 1% anhydrous silica and then heated at 60 C. for 3 hours in an air stream oven. The cured time-release components or microcapsules equivalent to 80 mg of diclofenac sodium were tested, and concentration of drug released in the dissolution fluid was determined by measuring the absorbance at 276 nm on an spectrophotometer.

Figure 3:
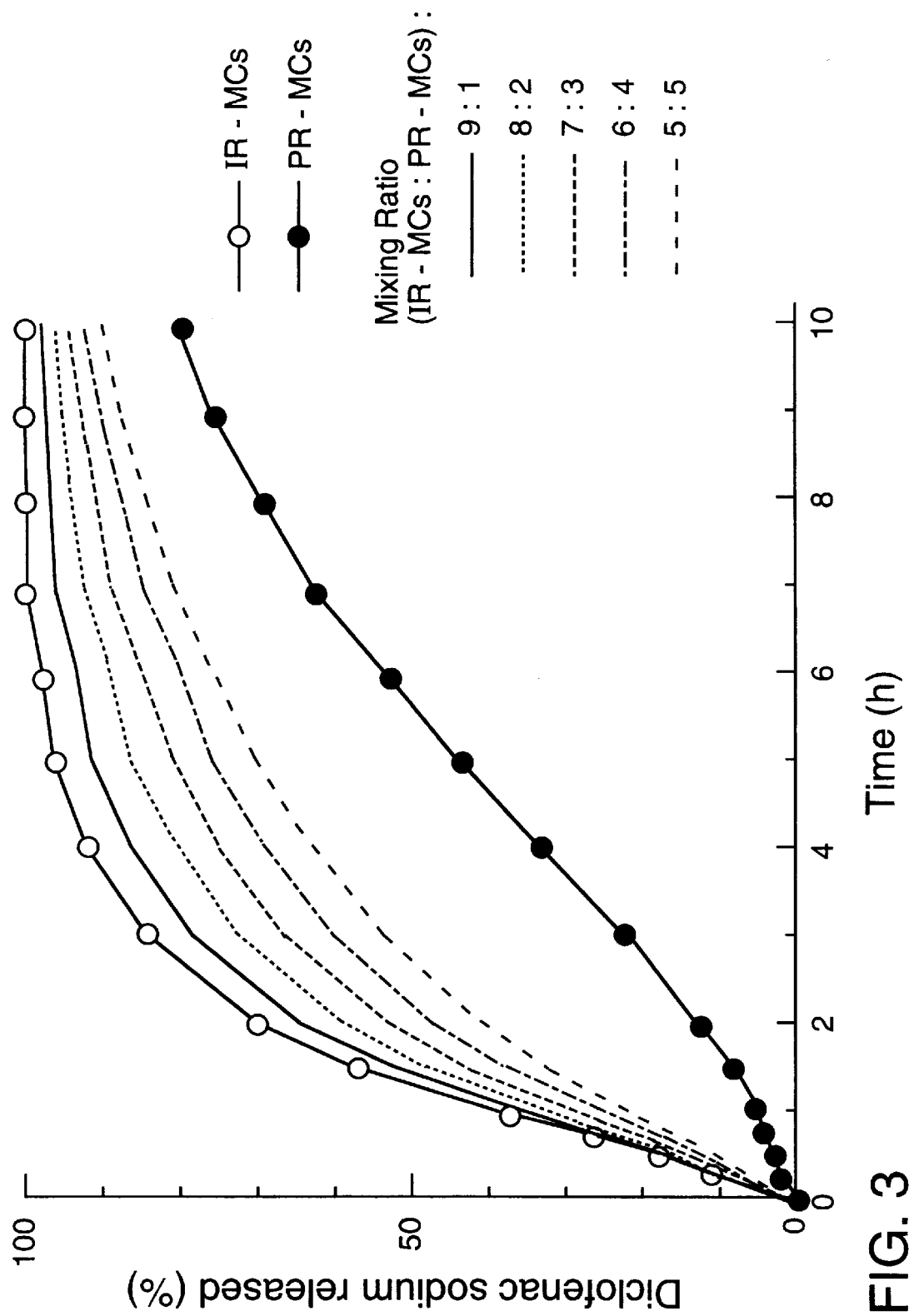
FIG. 3 is a plot of time versus percent release of the drug components in FIGS. 1 and 2 in dissolution fluid and the estimated release profiles on the combination of both microcapsules.

Release profiles of diclofenac sodium from the time-release components or microcapsules 20% and 50% coated with Eudragit RS-30D in JP XII disintegration 2nd fluid (pH 6.8) are shown in FIG. 3. Former and later were denoted as IR-MCs and PR-MCs, respectively. Release of drug from IR-MCs was fast and it completed within 5 hours. On the other hand, PR-MCs exhibited prolonged release over 10 hours, but there was a time lag with 1 hour at earlier stage of dissolution. Considering that diclofenac sodium undergoes extensive metabolism and it has a relatively short elimination half-life in plasma, release of drug from PR-MCs seems to slow and it may lead to the lowering of bioavailability of drug. Therefore, PR-MCs were combined with IR-MCs in order to increase the release rate. The release profiles on various mixing ratio of PR-MCs and IR-MCs shown by the other curves were estimated by calculating the weighted average of the amount of drug released from both microcapsules or time-release components.

The results were also shown in FIG. 3 by curves with no symbols. The mixing ratio of 7:3 gives the best results in obtaining prolongation of drug release.

In drug-layering process, particles containing a lesser amount of drug could be successfully prepared. Their high layering efficiency indicated that the drug particles adhered to the cores. Generally, spraying of drug suspension against fine particles frequently results in very low efficiency of layering in comparison to the case of spraying of drug solution. In the case of the present study, high hygroscopicity of diclofenac sodium seemed to contribute to increase of adhesion force of drug particles themselves.

The thickness of the drug-layer in the microcapsules or time-release components was estimated to be 17 $\mu$m under the assumption that the density of the drug was the same as that of hydroxypropylcellulose (HPC) used as binder (1.22 g/cm3) and that the drug and the binder were homogeneously coated on the spherical cores of 38 $\mu$m (mean of sieve openings used in preparing the cores). Theoretically, the diameter of the product without agglomeration should be 72 $\mu$m. This value was comparable to the mass median diameter of the produced drug-layered particles. This meant that agglomeration tendency of the spheres in drug-layering process was very low (2%) and calcium carbonate cores were discretely covered with binder and drug particles. Eudragit RS-30D, an aqueous acrylic latex, was chosen as a film-coating material for prolonged release and for environmental considerations. Dibutyl sebacate (DBS) was used as a lipophilic plasticizer to minimize the change of mechanical properties of Eudragit RS-30D coat induced by the leaching out of plasticizer from the coat during the dissolution process. To increase the drug content in the products, layering of a large amount of drugs was necessary.

Due to the physicochemical properties of diclofenac sodium; that is, its high water solubility and high hygroscopicity, however, incorporation of a larger amount of such drugs would induce a more rapid release. On the other hand, the thickness of the coating had to be as thin as possible to reduce a size-enlargement of products. It is known that solubility of diclofenac sodium in an aqueous medium is pH dependent; it is very slightly soluble in an acidic medium, though freely dissolves in a neutral or weak alkaline medium. Therefore, incorporation of an acidic compound into the time-release components or microcapsules was undertaken to lower the water-solubility of diclofenac sodium, leading to prolongation of drug release, consequently. Since a low molecular acidic compound such as organic acids would pass through the film coat itself during dissolution process, it was anticipated that its effect for lowering the solubility might become weak with time. Thus, Poly(methacrylic acid, ethyl acrylate) (commercially available under the designation Eudragit L30D-55), an acidic polymeric dispersion (pH 2.1–3.1), was introduced as a buffer between the drug-layer and the release-sustaining coat of Eudragit RS-30D.

Diclofenac sodium undergoes extensive metabolism and it has a relatively short elimination half-life in plasma. It is commonly said that to prolong release of drugs having such properties leads to the lowering of its bioavaiability. In practice, therefore, further optimization of the release profiles by some additional strategies, for example, saturation of the metabolic processes by the combination of time-release components or microcapsules having fast release profile with prolonged release time-release components or microcapsules as prepared here, will be used to avoid the lowering of the bioavailability and to get a well maintained plasma diclofenac concentration. Diclofenac sodium is usually used in 25, 50 and 75 mg doses, thus the suspension can be used in teaspoon quantity, depending on the drug load. If one takes 75 mg of the drug, which is maximum dose, and the dose as for the suspension is 300 mg/10 ml per one, the lower limit of drug content in the microcapsules becomes 25%. The drug content of the LR-MCs with 50% levels of the release-sustaining coat Eudragit RS-30D, which showed preferable prolonged drug release, was 28.9%. This value was sufficiently high to satisfy the above-mentioned dosage plan.

In summary, the prolonged release time-relemicrocapsuless or microcapsules containing diclofenac sodium applicable for suspensions were prepared by the Wurster process. The idea in preparing the microcapsules was to prolong the release of highly water-soluble diclofenac sodium while allowing the microcapsules to have about 100 $\mu$m of mass median diameter and a high content of the drug. Undercoating of an acidic polymer like Eudragit L30D on the drug-layered particles and subsequent coating of an aqueous latex like Eudragit RS-30D was effective to prolong release of the drug. The release rate was controllable by adjusting the thickness of the release-sustaining coat of Eudragit RS-30D. As a result, this permitted the formation of time-release components or microcapsules whose mass median diameter and drug content were about 100 $\mu$m and 30%, respectively. While the drug layer has been referred to as the drug, it will be appreciated that this layer will contain as active ingredients one or more drugs and may contain in addition other material known to those skilled in the art commonly employed in orally administrable drug form such as fillers, binders, coloring agents and other desired materials. It will be appreciated that the present invention has provided a method and associated time-release drug form which facilitates having the desired blood concentrations of the drug over time.

Whereas, particular embodiments of this invention have been described above for purposes of illustration, it will be evident to those skilled in the art that numerous variations of the details of the present invention may be made without departing from the invention as defined in the appended Claims.

What is claimed is:

1. A time-release orally administrable drug containing product comprising:
   a core;
   a drug secured to the exterior of said core;
   a first coating having limited permeability to water secured to the exterior of said drug; and
   a second coating, which is more permeable to water than said first coating, secured to the exterior of said first coating; wherein said first coating and second coating together comprise the time release components of said drug.

2. The drug containing product of claim 1 wherein said product is suspended in an aqueous medium.

3. The drug containing product of claim 1 wherein said product is in tablet form.

4. The drug containing product of claim 1 wherein said product is in capsule form.

5. The drug containing product of claim 1 wherein said first coating and said second coating effect time release of said drug within a patient over a maximum period of about 14 hours.

6. The drug containing product of claim 1 wherein the thickness of the first coating is about 1.30 to 4.60 microns and the thickness of the second coating is about 6.70 to 13.40 microns.

7. The drug containing product of claim 6, wherein said time-release components are of a substantially spherical configuration.

8. The drug containing product of claim 7, wherein said first coating has a diameter of about 60 to 77 microns.

9. The drug containing product of claim 8, wherein said core has a diameter of 19 to 57 microns.

10. The drug containing product of claim 7, wherein said product has a diameter of about 20 to 650 microns.

11. The drug containing product of claim 7, wherein said product has a diameter of about 50 to 250 microns.

12. The drug containing product of claim 9, wherein said product is in liquid suspension form.

13. The drug containing product of claim 12, wherein said first coating and said second coating effect time release of said drug in a patient over a maximum period of about 14 hours.

14. The drug containing product of claim 13 wherein said product dissolves sequentially in vivo in acid, neutral, and weak alkaline regions of the gastrointestinal tract.

15. The drug containing product of claim 14, wherein said first coating is an acidic dispersion polymer.

16. The drug containing product of claim 15 wherein said first coating is poly(methacrylic acid, ethyl acrylate).

17. The drug containing product of claim 13, wherein said second coating is a latex acrylic polymer.

18. The drug containing product of claim 17 wherein said second coating is Poly(methacrylic acid, ethyl acrylate).

19. The drug containing product of claim 17, wherein said core is selected from the group consisting of calcium carbonate, sugar, dextrose and nonpareil seeds.

20. The drug containing product of claim 13, wherein the thickness of said second coating can be altered to between about 6.70 and 13.40 microns depending on the desired length of time release.

21. A method of treating a patient with an orally administrable time-release drug comprising:
administering to said patient the time-release orally administrable drug containing product of claim 1.

22. The method of claim 21 wherein said drug containing product is suspended in an aqueous medium.

23. The method of claim 21 wherein said drug-containing product is in tablet form.

24. The method of claim 21 wherein said drug-containing product is in capsule form.

25. The method of claim 21 wherein said first coating and said second coating effect time release of said drug in a patient over a maximum period of about 14 hours.

26. The method of claim 21 wherein said drug-containing product is administered 2 to 4 times daily.

27. The method of claim 21 wherein said first coating has a thickness of about 1.30 to 4.60 microns and said second coating has a thickness of about 6.70 to 13.40 microns.

28. The method of claim 27 wherein said time-release components are of a substantially spherical configuration.

29. The method of claim 28 wherein said core has a diameter of 19 to 57 microns.

30. The method of claim 29 wherein said first coating has an exterior diameter of about 60 to 77 microns.

31. The method of claim 28 wherein said drug-containing product has a diameter of about 20 to 650 microns.

32. The method of claim 28 wherein said drug-containing product has a diameter of about 50 to 250 microns.

33. The method of claim 21 wherein said drug-containing product is in liquid suspension form.

34. The method of claim 31 wherein said drug-containing product is employed therapeutically.

35. The method of claim 31 wherein said drug-containing product is employed prophylactically.

36. The method of claim 31 wherein said drug-containing product is employed diagnostically.

37. The method of claim 34 wherein said drug in said drug containing product is an anti-inflammatory drug.

38. The method of claim 37 wherein said method is employed in the treatment of rheumatic disorders selected from the group consisting of osteoarthritis, rheumatoid arthritis and ankylosing spondylitis.

39. The method of claim 21 wherein said drug-containing product dissolves *in vivo* sequentially in acid, neutral and weak alkaline regions of the gastrointestinal tract.

40. The method of claim 39 wherein an acid polymeric dispersion coating is used as said first coating to prolong drug release.

41. The method of claim 40 wherein said core material is selected from the group consisting of calcium carbonate, sugar, dextrose, and nonpareil seeds.

42. The method of claim 41 wherein said first coating is a material which retards rapid passage of an acidic drug and water therethrough.

43. The method of claim 42 wherein said first coating is an aqueous dispersion of poly(ethyl acrylate, methyl methacrylate trimethylammonioethyl methacrylate chloride).

44. The method of claim 43 wherein said second coating is a latex acrylic polymer.

45. The method of claim 39 wherein the thickness of said second coating can be altered to between about 6.7 and 13.4 microns so as to achieve the desired time release rate for said drug containing product.

46. The method of claim 45 wherein said second coating is poly(methacrylic acid, ethyl acrylate).

* * * * *